(12) United States Patent
Rudischhauser et al.

(10) Patent No.: US 6,201,649 B1
(45) Date of Patent: Mar. 13, 2001

(54) METHOD FOR MOUNTING ROD LENSES IN AN ENDOSCOPE, AND ENDOSCOPE HAVING SUCH ROD LENSES

(75) Inventors: Jürgen Rudischhauser, Tuttlingen; Ulrich Kehr, Ostfildern, both of (DE)

(73) Assignee: Karl Storz GmbH & Co, KG (DE)

( * ) Notice: Subject to any disclaimer, the term of this patent is extended or adjusted under 35 U.S.C. 154(b) by 0 days.

(21) Appl. No.: 09/567,154

(22) Filed: May 9, 2000

Related U.S. Application Data (63) Continuation of application No. PCT/EP98/07252, filed on Nov. 12, 1998.

(30) Foreign Application Priority Data

Nov. 15, 1997 (DE) ................................................ 197 50 685

(51) Int. Cl.[7] .............................. G02B 7/02; G02B 3/00; A67B 1/00
(52) U.S. Cl. ......................... 359/808; 359/809; 359/811; 359/819; 600/101
(58) Field of Search ................................ 359/808; 8/809, 8/810, 811, 819, 710; 600/130, 101

(56) References Cited

U.S. PATENT DOCUMENTS

| | | | |
|---|---|---|---|
| 5,892,625 | * | 4/1999 | Heimer .................................. 359/665 |
| 5,999,344 | * | 12/1999 | Wolfsberg et al. ................... 359/819 |

FOREIGN PATENT DOCUMENTS

| | | |
|---|---|---|
| 722 587 | 12/1952 | (DE) . |
| 28 12 369 | 11/1978 | (DE) . |
| 3431631 C2 | 10/1990 | (DE) . |
| 264 523 A1 | 9/1993 | (DE) . |
| 37 30 094 | 9/1993 | (DE) . |
| 4438511 A1 | 10/1994 | (DE) . |
| 94 17 262 U | 3/1995 | (DE) . |
| 197 50 685 A1 | 11/1997 | (DE) . |

OTHER PUBLICATIONS

Roger S. Reiss, Precision Instrument Design Working Group, Jul. 1989, 1 pg.

* cited by examiner

*Primary Examiner*—Georgia Epps
*Assistant Examiner*—Saeed Seyrafi
(74) *Attorney, Agent, or Firm*—St. Onge Steward Johnston & Reens LLC (57) ABSTRACT

A method for mounting at least one rod lens in an interior of a tube has the following steps, i.e. selecting an outside diameter of said rod lens in that an airgap is created circumferentially between an outer side of said rod lens in an inner side of said tube, positioning said outer side of said rod lens at a defined radial spacing from said inner side of said tube by way of at least two centering aids and effecting an elastic adhesive join between said outer side of said rod lens and said inner side of said tube.

24 Claims, 5 Drawing Sheets

METHOD FOR MOUNTING ROD LENSES IN AN ENDOSCOPE, AND ENDOSCOPE HAVING SUCH ROD LENSES

CROSSREFERENCE OF PENDING APPLICATION

This is a continuation of pending international application PCT/EP 98/07252 filed on Nov. 12, 1998.

BACKGROUND OF THE INVENTION

The present invention relates to a method for mounting at least one rod lens in the interior of a tube belonging to an endoscope by immobilizing the rod lens in the interior of the tube at at least two points spaced axially apart from one another, having the following steps:

Selecting the outside diameter of the rod lens such that after introduction of the rod lens into the tube, an air gap is created circumferentially between the outer side of the rod lens and the inner side of the tube; and Positioning the outer side of the rod lens at a defined radial spacing from the inner side of the tube by way of at least two centering aids that engage at at least two points spaced axially apart from one another on the outer side of the rod lens, each centering aid having centering elements that are distributed uniformly around the circumference of the rod lens.

The invention further concerns an endoscope having a tube in whose interior at least one rod lens is immobilized at at least two points spaced axially apart from one another, the rod lens having an outside diameter which is dimensioned such that after introduction of the rod lens into the tube, an air gap is present between the outer side of the rod lens and the inner side of the tube; and the outer side of the rod lens being arranged at a defined radial spacing from the inner side of the tube.

A method of this kind, and a corresponding endoscope, are known from DE 34 31 631 C2.

Endoscopes are used generally in surgical practice to inspect body cavities and hollow organs. Endoscopes have an elongated tubular shaft in which components of an optical observation system are arranged. Also provided in the interior of the shaft are further devices, usually a light delivery device and optionally ducts for instruments, flushing liquids, or the like.

Light delivery is usually accomplished via light-conveying glass fibers.

The optical system of rigid endoscopes is usually received in a tube located inside the endoscope shaft. The essential constituents of the optical system are the lenses, rod lenses of the so-called Hopkins optical type being used, in particular, in endoscopes. The lenses and further constituents of the optical system, such as aperture stops, filters, and the like, are arranged along the tubular shaft axis; their task is to reproduce a clear image, with high resolution and high contrast, of as large a field of view as possible.

The most important prerequisite for this is precise arrangement of the lenses and the further components of the optical system with respect to one another in the interior of the tube belonging to the endoscope. The relative position of a lens is not variable, but precisely defined. Any shifting of the lenses relative to one another results in diminished image quality. Precise arrangement is often achieved by the fact that the outside diameter of a rod lens corresponds exactly to the open inside diameter of the tube, i.e. the lens is received without radial clearance.

Spacer sleeves, including a distal and a proximal terminating piece, placed between the lenses ensure axial positioning and immobilization of the lenses and optical components.

One problem is the fact that shocks occur when the endoscope is handled and especially when it is cleaned (for example during ultrasonic cleaning), causing the lenses to shift radially within the existing clearance and, in particular, causing abrasion at the contact surfaces between the outer side of the rod lenses and the inner side of the internal tube which adversely affects the optical imaging quality.

Endoscope shafts are very long as compared to their diameter: usual diameters are on the order of a few millimeters, and lengths on the order of several tens of centimeters. When rigid endoscopes are handled, bending torques act on the thin, long shafts and can cause breakage of the relatively long rod lenses made of glass materials.

One approach to immobilizing rod lenses in the interior of an endoscope while retaining a certain flexibility is described in U.S. Pat. No. 4,148,550, which corresponds to DE Unexamined Application 28 12 369.

The rod lenses provided therein are joined to one another in the interior of the endoscope by an additional inner tube. This inner tube has longitudinally extending slits in the region in which it bridges the ends of two adjacent rod lenses that are spaced apart from one another.

The rod lenses sit tightly, without radial clearance, in the inner tube, i.e. the outside diameter of a lens corresponds to the open inside diameter of the inner tube. The rod lenses are either simply jammed in place in the tube, or are bonded using adhesive. It is proposed for this purpose to use, for example, an adhesive that can be activated by heat treatment or UV radiation.

The ability to bend the tubular shaft within certain limits without thereby breaking the rod lenses is achieved by way of the slits of the inner tube. The inner tube can buckle slightly in the region of the slits, i.e. in the region between two adjacent rod lenses.

Because bending is possible only in the region of the slits of the inner tube, the minimum possible bending radius is very large. This is true in particular if the spacings between the rod lenses are very small compared to the rod lens length. Uniformly curved bending of the tubular shaft is not possible. If bending torques act directly in the region of the rod lenses and result in bending of the outer endoscope shaft, the rod lenses can still break. Bending torques of this kind acting in single-point fashion can occur if an endoscope strikes against an edge or is dropped while being handled.

DE 44 38 511 A1 (which corresponds to German utility model DE 94 17 262 U) describes an endoscope in which damage to the rod lenses is to be prevented by surrounding them coaxially, inside the tube, with a reinforcing member that, in contrast to the rod lens, is produced from a high-strength material such as metal or ceramic. The reinforcing member is shorter than the rod lens itself. This once again results in the difficulty that as the length of the reinforcing member increases, uniform curved bending of the tubular shaft is prevented. But the shorter the reinforcing member, the less stable the mounting of the rod lens inside the tube in terms of tilting. The purpose of the reinforcing lens is also not to increase the radial spacing between the rod lens and the tube. Instead, the reinforcing member is intended to protect the central region of the rod lens, in which stress is concentrated when a bending load is applied.

DE 34 31 631 C2, already mentioned above, describes a rod lens mount in which the rod lenses are mounted inside the tube by way of two spacer rings spaced axially apart from one another. As a result, the rod lenses are located at a radial spacing from the inner surface of the tube. This spacing creates a clearance, so that in response to a bending stress the tube can bend independently of the rod lens.

According to this document, however, the spacer rings are made of materials such as, for example, metal, in particular brass, or plastic, in particular hard plastic and the like. Because hard materials of this kind are used, the rod lenses are very rigidly joined to the tube despite the existence of a radial spacing. Correspondingly, bending loads of the tube are also transferred, largely un-damped, to the rod lenses. Damage to the rod lenses due to bending torques is therefore not reliably prevented despite the existence of the radial spacing.

It is known from a publication in OE Reports No. 67, July 1989, page 13, published by SPIE, to adhesively bond lenses in a mount using centering elements, in the form of centering screws, that are to be removed after adhesive bonding.

DE 37 30 094 C2 has disclosed centering elements that are distributed uniformly over the circumference of a lens.

DE-A-722 587 has disclosed two centering aids spaced axially apart from one another, and DD 264 523 A1 has disclosed methods for coaxial adhesive bonding-in of lenses.

Against the background of this existing art, it is the object of the present invention to create a method and an endoscope of the type cited initially in which any transfer of bending forces to the at least one rod lens is reduced even further, while at the same time the rod lens is immobilized in secure and correctly positioned fashion in the interior of the tube.

SUMMARY OF THE INVENTION

This object is achieved according to the present invention, in the case of the method cited initially, in that an elastic adhesive join is effected between the outer side of the rod lens and the inner side of the tube.

The object is further achieved, in the case of the endoscope cited initially, in that the outer side of the rod lens is immobilized on the inner side of the tube with elastic adhesive points using adhesive.

A first advantage of the method according to the present invention is the fact that because of the smaller outside diameter of the rod lens as compared to the inside diameter of the tube, the rod lens can be effortlessly introduced into the tube. The tube that is provided can be the tubular shaft of the endoscope itself, or a further inner tube of the endoscope that is introduced into the tubular shaft of the endoscope only after installation of the lenses.

Positioning the rod lens centeredly in the tube with the help of the centering aids ensures that a homogeneous air gap, i.e. a defined radial spacing, is created between the outer side of the rod lens and the inner side of the tube. Because of the axial spacing of the centering points on which the centering aids engage, tilting of the rod lenses inside the tube during installation is reliably prevented, so that the rod lens can be exactly aligned along the optical axis. Depending on the length of the rod lens that is to be installed, two, three, or even more centering aids can be provided here, respectively spaced axially apart from one another.

After centering of the rod lens, an elastic adhesive join is effected between the outer side of the rod lens and the inner side of the tube; the adhesive to be used here does not completely fill up the air gap, but rather is applied only at at least two adhesive points spaced axially apart from one another. Here again, depending on the rod lens length, several adhesive points located respectively at axial spacings from one another can be provided. Two adhesive points spaced axially apart from one another, within the meaning of the present invention, also exist if one adhesive point extends axially and longitudinally to such an extent that tilting is prevented. This can be done with relatively short rod lenses; in that case the two opposite outer end regions of a longitudinally extending adhesive point of this kind would be two axially distanced points.

The assemblage of one or more rod lenses produced by way of the method according to the present invention in the interior of the tube has the advantage that because of the adhesive points, the rod lenses are secured against both axial and radial shifting, in particular against tilting. Application of the adhesive at the adhesive points thus ensures correctly positioned immobilization of the rod lenses, and they therefore yield consistent imaging quality.

As a result of the air gap that is provided, the outer side of the rod lens is not in direct contact with the inner side of the tube, so that even a severe shaking stress (for example, when the endoscope is cleaned ultrasonically), does not produce any abrasion that could negatively affect the optics.

The air gap moreover ensures, together with the adhesive points according to the present invention, the desired flexibility of the assemblage of tube and lens in response to loads, in particular bending torques. This is because when bending of the tube occurs, the air gap, together with the adhesive points that create an elastic join between lens and tube, make it possible initially for only the tube to bend. As a result, initially only a small bending torque is exerted on the rod lens which is made of glass and therefore can withstand only a limited load—and that load does not increase until the bending of the tube is so great that its inner side touches the outer side of the rod lens.

The tube can thus bend in curved fashion, since an appropriate clearance exists between rod lens and tube in the form of the air gap.

Breaking or chipping of the rod lens in response to the usual loads on a rigid endoscope, which are exerted on the endoscope shaft both during handling (e.g. during surgery or when the endoscope is set down) and during cleaning (e.g. due to contact with other equipment being cleaned), is thus reliably prevented.

The air gap together with the adhesive points additionally ensures protection of the lens from externally applied forces, since the adhesive join is elastic and can therefore damp impacts. The risk of breaking the rod lenses is thus considerably decreased, even if the endoscope is set down roughly or even dropped.

The endoscope according to the present invention has the advantage that its rod lenses are securely immobilized, so that axial or radial shifts are prevented. At the same time, bending of the tubular shaft of the endoscope is possible to a certain extent, specifically because of the provision, between the outer side of the rod lens and the inner side of the tube, of an air gap that is bridged only by the elastic adhesive points. The tube can thus bend to a certain extent without allowing the bending torques to act on the rod lens. Breakage of the rod lens while the endoscope is being handled and cleaned is therefore prevented.

In addition, because of the provision of the air gap there is no direct contact between the outer side of the rod lens and the inner side of the tube, so that even a shaking stress, for example during cleaning, would not produce any abrasion that might adversely affect imaging quality.

The object of the invention is thereby completely achieved.

The exact dimensions of the radial spacing or air gap provided between the outer side of the rod lens and the inner side of the tube can be different depending on the desired application. The person skilled in the art can dimension the spacing taking into account the length of the rod lens or multiple rod lenses (which can also have different lengths within a single tube), the material from which the tube is made, and the shape and size of the adhesive points and the particular adhesive used.

In a preferred embodiment of the invention, the radial spacing between the outer side of the rod lens and the inner side of the tube is selected so that it lies in the range from approximately 0.05 to 0.3 mm, preferably in the range of approximately 0.1 mm.

With a spacing of this kind, it is easy both to introduce the rod lens into the tube and to effect the adhesive join, since sufficient clearance is present for introduction without requiring the adhesive points to bridge too large a radial spacing, which might make the adhesive join unstable.

In a further embodiment, positioning is accomplished with at least three centering elements, arranged with a circumferential offset of 120°, for each centering aid.

The advantage of this feature is that the rod lens is supported in particularly secure fashion, so that shifting or tilting of the rod lens is no longer possible.

It is understood that depending on the outside diameter of the rod lens, more than three centering elements may also be provided in order to support the lens.

In a further embodiment, the centering elements are left in the assemblage after the adhesive join has been effected.

For this purpose, the centering elements can be provided as spacers that are present in the form of spacer pieces of greater or lesser size, or radially or axially extending strips. They can be made of any desired material, for example plastic.

It is advantageous in this context that removal of the centering elements after installation is not necessary, which considerably simplifies the method according to the present invention. In the event that the spacers are made of an elastic material, they moreover provide additional protection for the lens against applied forces.

In a further embodiment, elongated, in particular cylindrical, metal or plastic parts are selected for positioning, and are set in place extending axially between the inner side of the tube and the outer side of the rod lens; and they are removed again after the adhesive join is effected or they are left in the assemblage.

In a preferred embodiment, radially extending centering pins, which pass through openings in the wall of the tube and are removed after the adhesive join is effected, are used for positioning.

The advantage of this feature is that positioning and centering of the rod lens can be performed particularly precisely, since the outer side of the rod lens can be accessed directly through the openings in the wall of the tube even after the rod lens has been completely introduced into the interior of the tube. The rod lens thus can first be brought into its exact axial position, and then its radial or centered position can be adjusted. A further advantage of this feature is that the centering elements can be manipulated from outside, which considerably facilitates the centering operation.

In an embodiment, at least one opening in the wall of the tube, through which the adhesive for effecting the adhesive join can be placed between the tube and rod lens, is provided at each adhesive point.

The considerable advantage of this feature is that the adhesive need not be delivered until the centering operation is complete and the rod lens has been precisely positioned in the interior of the tube. A further advantage here is that the adhesive can be applied through the opening at a defined point, so that it is not distributed to undesired locations by subsequent further axial or radial shifting of the rod lens, thus adversely affecting the tolerance of the assemblage of tube and rod lens in terms of bending loads.

In a further embodiment, three openings distributed uniformly around the circumference of the tube, through which the adhesive for effecting the adhesive join between the tube and the rod lens is applied in the form of adhesive dots, are provided.

The substantial advantage of this feature is that the rod lens is immobilized in the interior of the tube in such a way that any axial or radial shifting of the lens is reliably prevented. The flexibility of the assemblage is guaranteed as a result of the elasticity of the adhesive applied as dots.

A further advantage of this feature is that pressure compensation between the two axial ends of the tube is possible. This is because differences in air pressure between the two ends can result in longitudinal forces that place loads on the adhesive points.

In a further embodiment, the adhesive for effecting the adhesive join between the tube and rod lens is applied through the opening in the form of an adhesive ring that encloses the circumference of the rod lens in the region of the adhesive point.

The advantage of this feature is that the outer side of the rod lens is adhesively bonded circumferentially to the inner side of the tube in the region of the adhesive point, and is thereby immobilized in particularly secure fashion. Tilting of the rod lens in the interior of the tube in any direction is completely prevented.

In a further embodiment, the centering pins pass through those openings through which the adhesive is also applied, the outer side of the centering pins being made of a material that repels the adhesive or being coated with such a material; and they can be removed again from the assemblage after the adhesive join has been effected.

The advantage of this feature is that no additional holes in the wall of the tube need to be provided for application of the adhesive. The centering pins can thus first be passed through the openings in order to center the rod lens, and then the adhesive is introduced through the same openings. The adhesive can then cure, and only at that time are the centering pins withdrawn from the assemblage.

In a further embodiment of the invention, centering pins that have conical tips are used.

The advantage of this feature is that the centering pins can be pulled particularly easily out of the cured adhesive.

In an alternative embodiment of the method according to the present invention, adhesive dots that expand by activation, or that also attempt to assume a spherical shape due to surface tension, are applied as centering elements either onto the outer side of the rod lens or onto the inner side of the tube.

The considerable advantage of this embodiment is that in this case the centering elements have a dual function, on the one hand of centering and on the other hand of effecting the adhesive join. This additionally simplifies the method according to the present invention, since once again openings do not need to be provided in the wall of the tube either for introducing the centering elements or for applying the adhesive.

The adhesive dots can be applied at desired positions on the outer side of the rod lens or the inner side of the tube, the applied adhesive having a radial extension dimensioned such that a majority of the air gap between the outer side of the rod lens and the inner side of the tube is bridged when the rod lens is introduced into the tube. Sufficient clearance is still present, however, to allow easy introduction of the rod lens into the tube. Upon insertion of the rod lens into the tube, the rod lens is then "automatically" centered due to the convexity of the adhesive dots. The clearance remaining between the adhesive dot and, for example, the inner side of the tube is filled up by the adhesive only when it is activated, because of its expansion that then occurs, so that ultimately an immovable join is produced through the intermediary of the adhesive dot between the outer side of the rod lens and the inner side of the tube.

Preferably, activation of the adhesive is accomplished by heat treatment.

A heat treatment of this kind is particularly easy to perform. The temperature necessary therefor is above the temperature necessary for sterilizing the endoscope.

Depending on the activatable adhesive used, however, activation can also be accomplished by UV irradiation or other suitable actions.

In a preferred embodiment, the adhesive dots are surrounded by a material that serves as a barrier.

This material can surround the adhesive dots, for example, in annular fashion; a material repelling the adhesive can also be used.

The advantage of this feature is that the expansion of the adhesive following its application is laterally limited, and can occur substantially only in the radial direction.

In a further embodiment of the invention, elastic centering elements that are adhesively bonded to the inner side of the tube are applied on the outer side of the rod lens.

The advantage of this feature is that the centering elements are already themselves formed as a constituent of the elastic adhesive join. The elastic centering elements are then adhesively bonded to the inner side of the tube, and the globally elastic adhesive join between the inner side of the tube and the outer side of the rod lens is thereby effected.

In a further embodiment of the invention, in the case of a rod lens configured as a dog-bone lens having radial enlargements, the adhesive join is applied adjacent to the enlargement.

So-called "dog-bone" lenses, which are usually equipped with radial enlargements at the ends, are used in many endoscopes. The radial dimension of the lens is greater in the region of the enlargement than between the enlargements. If the elastic adhesive join is then applied in the region of the enlargement, considerable bending of the tube between these two adhesive points, i.e. between the radial enlargements, can still occur without adversely affecting the dog-bone lens, so that the invention is also applicable to such designs under the aforesaid conditions.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

Further advantages and embodiments of the invention are explained below with reference to the appended drawings, in which.

DETAILED DESCRIPTION OF PREFERRED EMBODIMENTS

Figure 1:
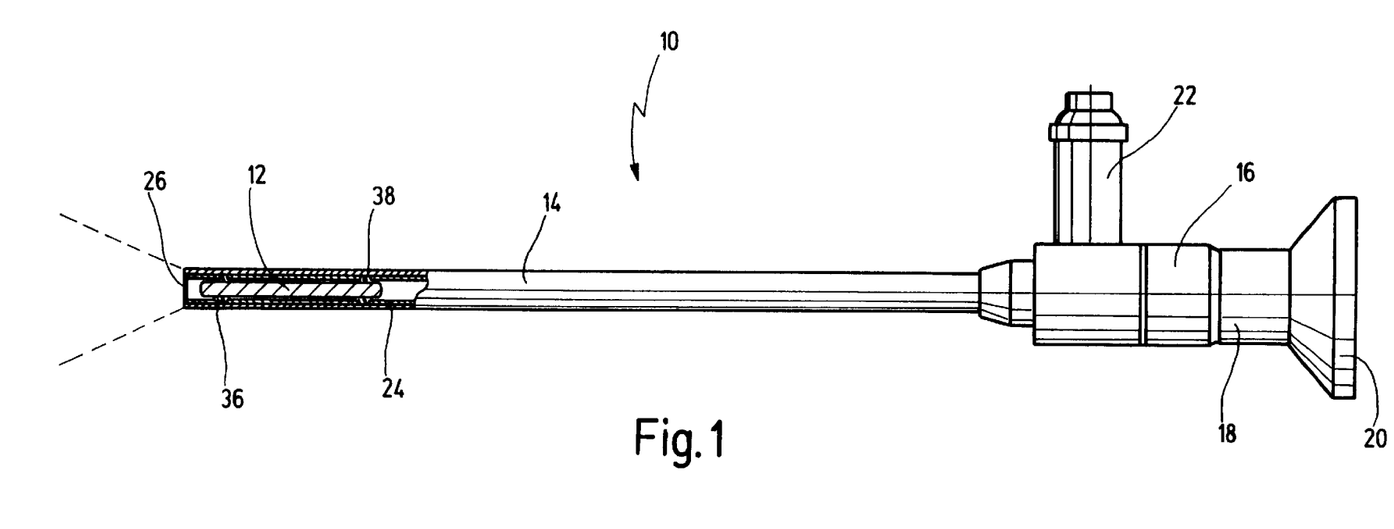
FIG. 1 shows a partially cutaway side view of an endoscope according to the present invention.

In an endoscope shown in FIG. 1, which is labeled in its entirety with the reference number 10, the method according to the present invention was used to install a rod lens 12 in the interior of endoscope 10.

Endoscope 10 has an elongated tubular shaft 14 at whose proximal end a housing 16 is arranged. An eyepiece 18 having an eyepiece cup 20 is provided in housing 16.

An optical system, which also includes rod lens 12, is received in tubular shaft 14 of endoscope 10. Together with further lenses, aperture stops, filters, and the like (not shown here), the optical system serves to bring to the proximal end an image sensed at the distal end. Also arranged for that purpose in tubular shaft 14 is a light-conveying system (not described in further detail here) in the form of glass fibers that are connected, via an extension 22 leading out from housing 16, to a light source (not shown here).

Arranged in the interior of tubular shaft 14 is an inner tube 24 inside which rod lens 12 and the further constituents (not shown) of the optical system are arranged.

A window 26 at the distal end of tube 24 forms a sealed closure of the distal end of tube 24, through which image information enters the optical system. If tube 24 cannot be hermetically sealed due to the adhesive openings or alignment openings discussed below, an intermediate tube (not shown here), which is then closed off sealingly by window 26 instead of tube 24, is provided.

Figure 2:
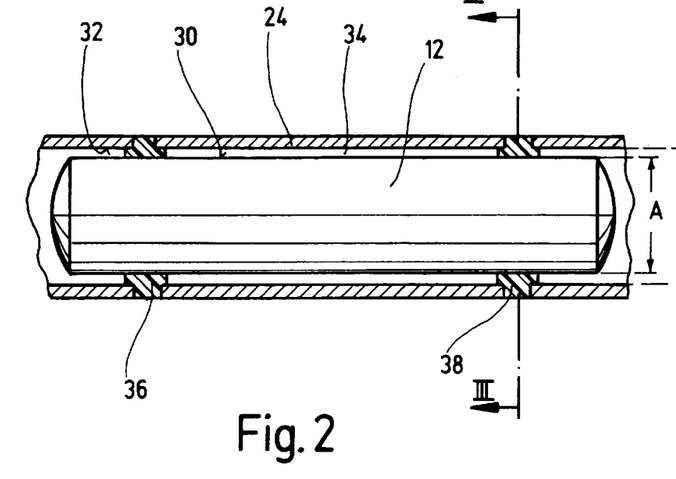
FIG. 2 shows a partial longitudinal section through an endoscope as shown in FIG. 1, specifically in the region of an assemblage of a tube and a rod lens.
Figure 3:
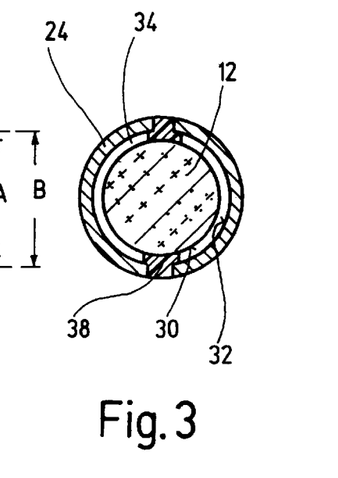
FIG. 3 shows a cross section along line III—III in FIG. 2.
Figure 4:
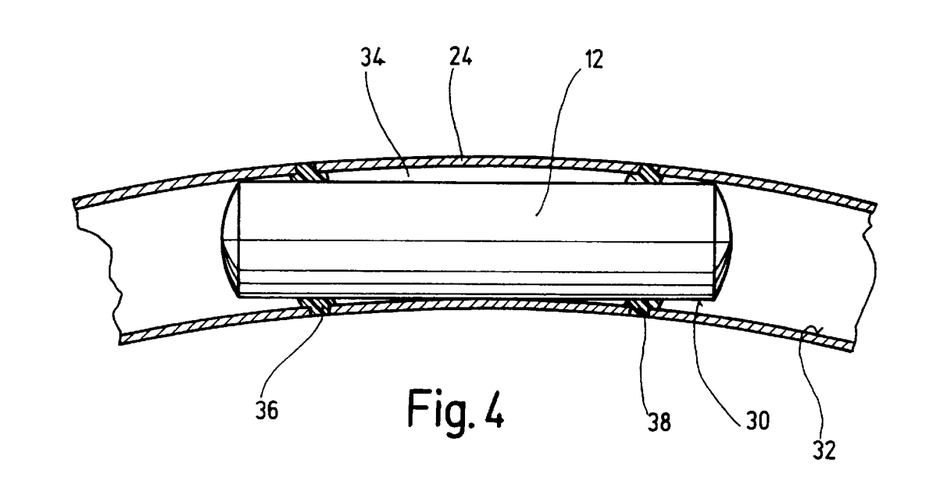
FIG. 4 shows a portion corresponding to FIG. 2, the tube being bent as a result of loads.

FIGS. 2 through 4 depict, in enlarged fashion, a portion of tube 24 having rod lens 12 arranged in its interior.

It is clearly evident from these representations that outside diameter A of rod lens 12 is smaller than the open inside diameter B of tube 24, so that a radial spacing or air gap 34 is present between outer side 30 of rod lens 12 and inner side 32 of tube 24. Outer side 30 of rod lens 12 has no direct contact with inner side 32 of tube 24, but instead is immobilized centeredly inside tube 24 by way of adhesive dots 36 and 38.

It is understood that the size relationships are not shown here at exact scale. Above all, the representation of air gap 34 and of adhesive dots 36 and 38 is greatly enlarged for reasons of clarity.

In the exemplary embodiment shown in FIGS. 2 through 4, rod lens 12 is mounted by way of a total of four adhesive dots 36. Each two adhesive dots 36 are distributed uniformly over the circumference of rod lens 12, i.e. arranged at a 180$i$ offset. In addition, the two adhesive dots 36 and 38 are spaced axially apart from one another.

By way of adhesive dots 36 and 38, rod lens 12 is immobilized in correctly positioned fashion in the interior of tube 24 so that no axial shifting or tilting of rod lens 12 is possible.

The flexibility of the assemblage in response to bending loads brought about by the coaction of air gap 34 with adhesive dots 36 and 38 is evident from FIG. 4. This shows that it is possible for tube 24 to bend in curved fashion to a certain degree without exposing rod 12 to a large bending load. The reason is that, because of air gap 34 and the elasticity of adhesive dots 36 and 38, it is possible for tube 24 to bend over the entire length of rod lens 12, adhesive dots 36 and 38 being able to deform to a certain extent.

Only beyond the degree of bending of tube 24 shown in FIG. 4, i.e. when inner side 32 of tube 24 touches outer side 30 of rod lens 12, is any bending load exerted on rod lens 12 as well.

It is understood that instead of adhesive dots 36 and 38 it is also possible to provide adhesive rings which enclose rod lens 12 circumferentially in the region of the adhesive points.

A further embodiment of the assemblage of tube 24 and rod lens 12, with reference to which the method according to the present invention for installing these components will be explained, is shown in FIGS. 5 through 10.

With this method, rod lens 12 is joined, at two points spaced axially apart from one another, by way of sets of at least two adhesive dots 36 and 38 distributed around the circumference of the rod lens in the interior of tube 24. The use of sets of at least two circumferentially distributed adhesive dots 36 and 38 allows particularly secure immobilization of the rod lens in the interior of the tube.

To install rod lens 12, it is first slid into tube 24, which is easily done because of air gap 34, which is on the order of 0.1 mm. To position rod lens 12 centeredly in the interior of tube 24, i.e. in order to create a defined spacing between outer side 30 of the rod lens and inner side 32 of the tube, centering aids which comprise multiple centering elements, and of which various embodiments are shown in FIGS. 7 through 10, are provided.

Figure 7:
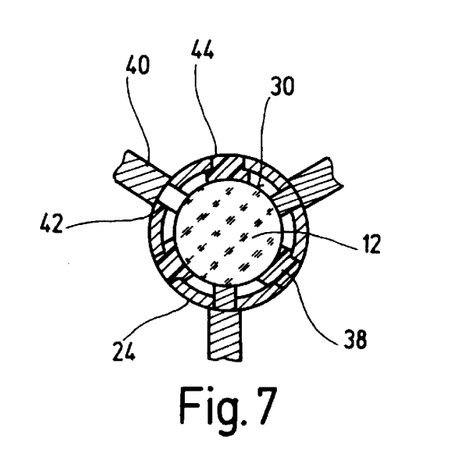
FIGS. 7 through 10 show cross sections through further embodiments of an assemblage according to the present invention.

In the case of the embodiment shown in FIG. 7, centering elements in the form of centering pins 40 are introduced through openings 42 of the wall of tube 24. The three centering pins 40 distributed uniformly over the circumference of rod lens, which engage through openings 42 in outer side 30 of rod lens 12, constitute a centering aid. In order to allow precise positioning of rod lens 12, two centering aids spaced axially apart from one another are provided.

Once rod lens 12 has been positioned by way of the centering aids at the desired spacing from inner side 32 of tube 24, the adhesive join between outer side 30 of rod lens 12 and inner side 32 of tube 24 is effected. This is done by applying adhesive in the form of adhesive dots 36, 38 through further openings 44 that are also distributed uniformly around the circumference of rod lens 12. Each adhesive dot 36, 38 fills up opening 44 in the wall of tube 24, and bridges, in a limited region, air gap 34 between outer side 30 of rod lens 12 and inner side 32 of the tube.

When the adhesive has cured, centering pins 40 can be withdrawn from openings 42 of the wall of tube 24.

Figure 5:
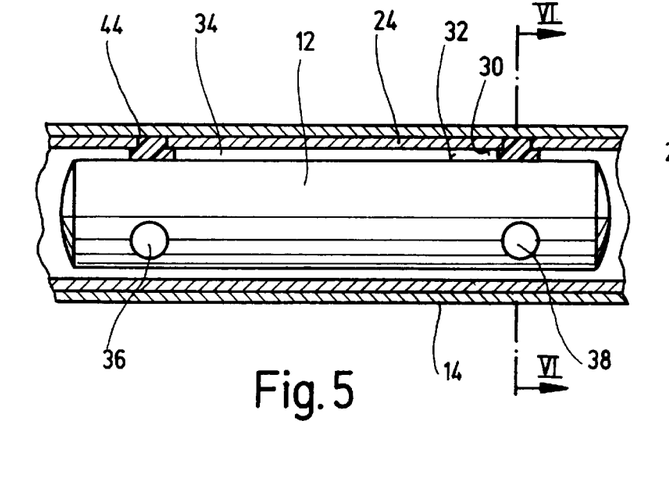
FIG. 5 shows a portion of a further embodiment of an assemblage according to the present invention, in longitudinal section.
Figure 6:
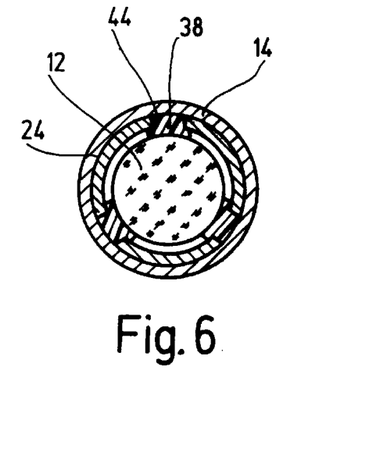
FIG. 6 shows a cross section along line IV—IV.

This assemblage can then be slid into tubular shaft 14, shown in FIGS. 5 and 6, of endoscope 10.

Figure 8:
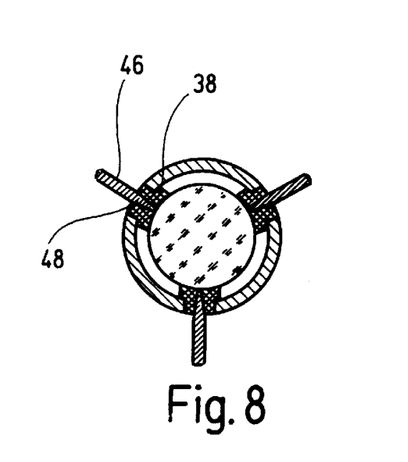

A further embodiment of the centering aid is illustrated in FIG. 8.

Centering pins 46 shown here engage onto the lens through openings 44 that are provided for application of the adhesive. Once rod lens 12 has been positioned centeredly, with the aid of centering pins 46, in the interior of tube 24, adhesive in the form of adhesive dots is applied through openings 44. This can be done without difficulty because, in the exemplary embodiment shown in FIG. 8, centering pins 46 are thinner than openings 44 and moreover have conical tips 48. To ensure that centering pins 46 can easily be removed again once the adhesive has cured, they can be made of an adhesive-repelling material or coated with such a material.

Figure 9:
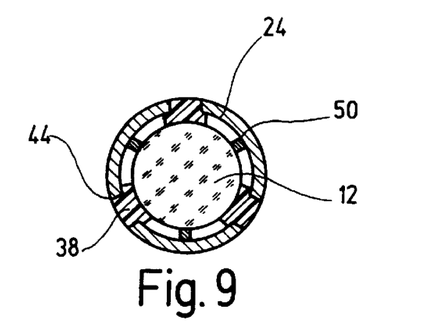
Figure 10:
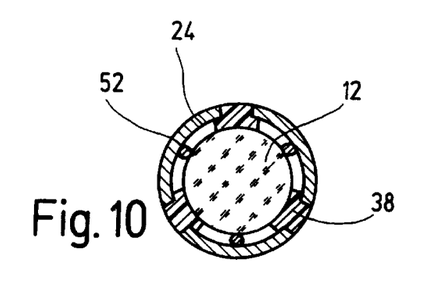

The centering aids provided in FIGS. 9 and 10 do not necessarily need to be removed from the assemblage after installation.

In FIG. 9, the centering aids are present in the form of three spacers 50, distributed circumferentially around rod lens 12, that can be provided either as spacer pieces or as axially extending strips that are made, for example, of plastic. Spacers 50 can be slid into tube 24 simultaneously with the lens. In this exemplary embodiment, it is not necessary either to remove spacers 50 after the application of adhesive dots 38 or to provide openings 44 for the centering aids in the wall of tube 24.

The centering aid shown in FIG. 10 is present in the form of axially extending elongated cylindrical bodies 52 that are distributed uniformly over the circumference of rod lenses 12. After adhesive dots 38 have been applied and have cured, cylindrical bodies 52 either can remain in the assemblage or can be withdrawn.

An alternative embodiment of the installation method according to the present invention is shown in FIGS. 11 through 16. In this embodiment, it is not necessary to provide openings in the wall of tube 24. The reason is that with this embodiment, centering of rod lens 12 is accomplished by way of adhesive dots 54 and 56 themselves. This is done by using an adhesive that can expand or can assume a spherical shape upon activation.

Figure 11:
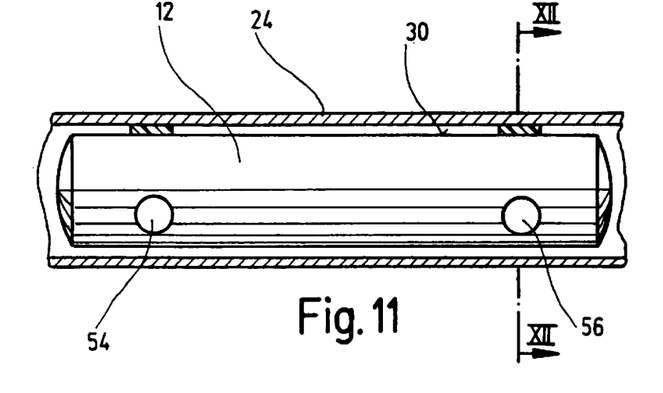
FIG. 11 shows a portion of an alternative embodiment of an assemblage according to the invention, in longitudinal section.
Figure 12:
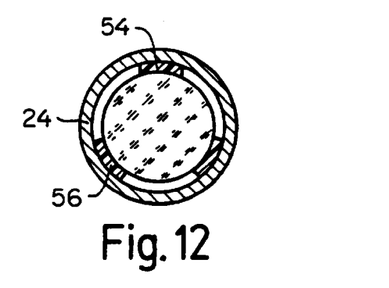
FIG. 12 shows a section along line XII—XII of FIG. 11.

For example, adhesive dots 54 and 56 can first be applied onto outer side 30 of rod lens 12 even before rod lens 12 has been slid into tube 24.

The distribution of adhesive dots 54 and 56 is arbitrary, but must be accomplished at at least two points spaced axially apart from one another. In order to allow maximally secure immobilization of the rod lens, preferably three adhesive dots 54, 56, distributed over the circumference of rod lens 12, are applied at two points spaced axially apart.

After the application of adhesive dots 54, 56 onto outer side 30 of rod lens 12, rod lens 12 is introduced into tube 24.

Figure 13:
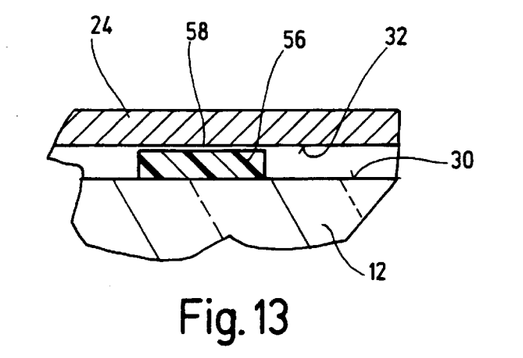
FIG. 13 shows an enlarged portion of the embodiment of FIG. 11, specifically in the region of an adhesive point before activation of the adhesive.

It is evident from FIG. 13 that adhesive dot 56 is radially elevated from surface 30 of rod lens 12, but a small gap 58 nevertheless remains open between adhesive dot 56 and inner side 32 of tube 24 to allow rod lens 12 to be slid in.

Figure 14:
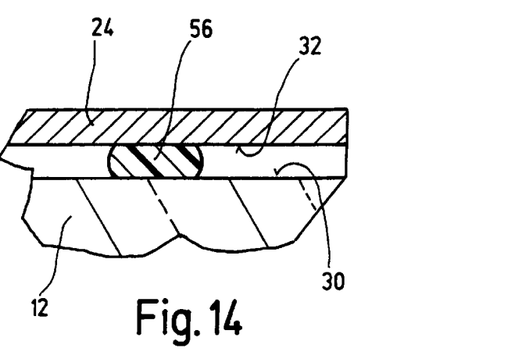
FIG. 14 shows the portion of FIG. 13 after activation of the adhesive.

The adhesive is then activated, for example by heat treatment, thus causing it to expand or deform, or to attempt as a result of surface-tension forces to assume a spherical shape (see FIG. 14). As a result, gap 58 fills up with adhesive in the region of adhesive dot 56, and adhesive dot 56 adhesively bonds inner side 32 of tube 24 to outer side 30 of rod lens 12, thus creating an immovable join.

Figure 15:
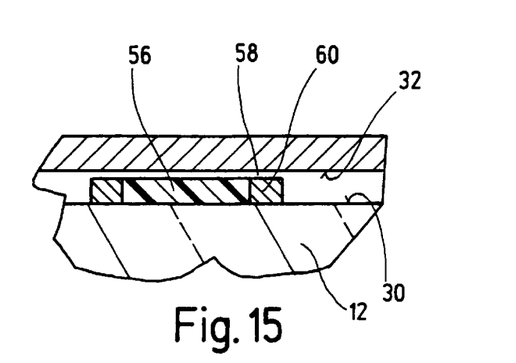
FIG. 15 shows a portion, corresponding to the representation of FIG. 13, of a further embodiment before activation of the adhesive.
Figure 16:
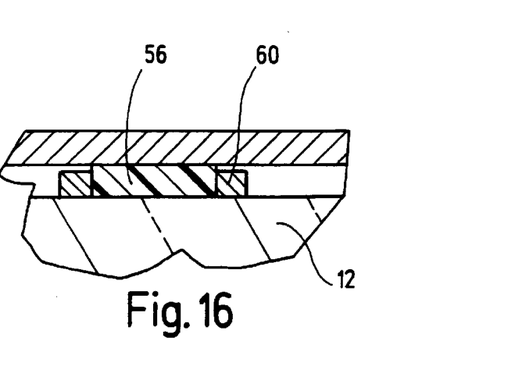
FIG. 16 shows the portion in FIG. 15 after activation of the adhesive.

In order to limit the expansion of the adhesive dots, they can be surrounded by a barrier, for example in the form of a spacer ring 60 as shown in FIGS. 15 and 16. Spacer ring 60 prevents the adhesive from becoming laterally distributed over larger surfaces of outer side 30 of rod lens 12 upon activation, causing it instead to expand substantially radially.

As shown in FIG. 16, after activation of the adhesive an adhesive dot 56 effects the join between inner side 32 of tube 24 and outer side 30 of rod lens 12.

Figure 17:
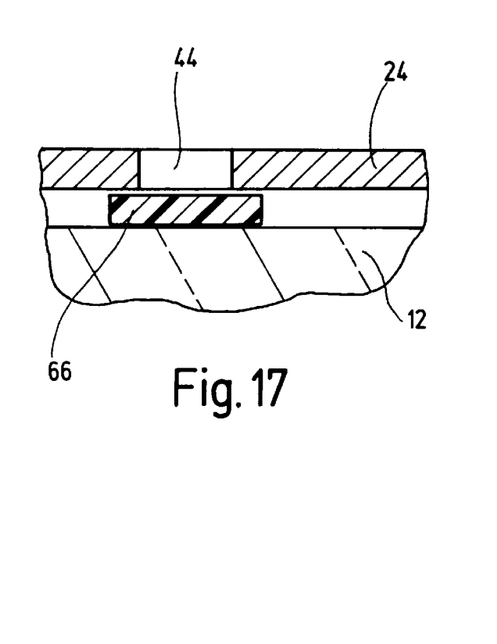
FIG. 17 shows a portion, comparable to the representation of FIG. 13, of a further embodiment having elastic centering elements.
Figure 18:
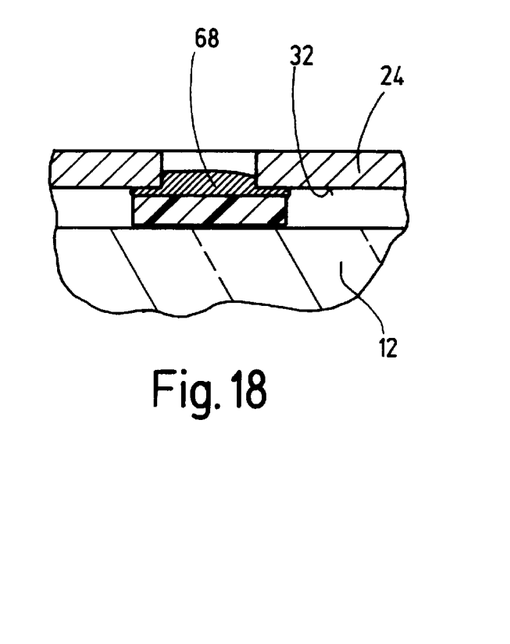
FIG. 18 shows the representation of FIG. 17 after the adhesive join has been effected.

In the case of the exemplary embodiment shown in FIGS. 17 and 18, elastic centering elements 66—which can be dot-shaped as described above, or of elongated or annular shape—are applied on the outer side of rod lens 12. These elastic centering elements provide correct positioning of lens 12 in tube 24. To effect the adhesive join, adhesive 68 is introduced through an opening 44 in tube 24 and then constitutes a join between elastic centering element 66 and inner side 32 of tube 24. This, too, then results overall in an elastic adhesive join between the outer side of rod lens 12 and inner side 32 of tube 24.

Figure 19:
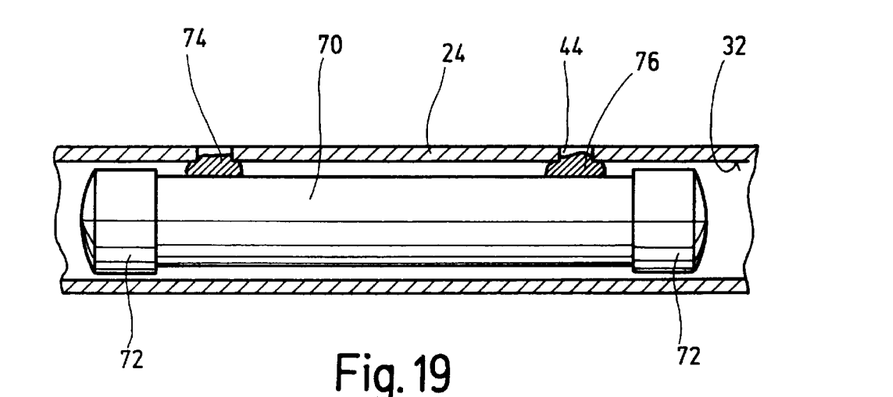
FIG. 19 shows a partial longitudinal section of an endoscope in which a dog-bone lens is installed.

FIG. 19 shows an embodiment of a rod lens as a dog-bone lens 70 that is equipped with enlargements 72 at the ends. Dog-bone lens 70 is joined, as described for example in conjunction with FIG. 2, to tube 24 via adhesive dots 74 and 76, so that the outer side of dog-bone lens 70 is thus joined via an elastic adhesive join to inner side 32 of tube 24. Referring to FIG. 4, it is evident therefrom that the essential bends take place between the adhesive dots. If, as shown in FIG. 19, adhesive dots 74 and 76 are located adjacent to enlargements 70 and 72, relatively pronounced bending of tube 24 can thus take place between adhesive dots 74 and 76, and then correspondingly between enlargements 72, as indicated in FIG. 4.

What is claimed is:

1. A method for mounting at least one rod lens in an interior of a tube belonging to an endoscope by immobilizing said rod lens in said interior of said tube at at least two points spaced axially apart from one another, said method having the following steps:

selecting an outside diameter of said rod lens such that after an introduction of said rod lens into said tube, an air gap is created circumferentially between an outer side of said rod lens and an inner side of said tube;

positioning said outer side of said rod lens at a defined radial spacing from said inner side of said tube by way of at least two centering aids engaging at at least two points spaced axially apart from one another on said outer side of said rod lens, each centering aid having centering elements that are distributed uniformly around a circumference of said rod lens, and effecting an elastic adhesive join between said outer side of said rod lens and said inner side of said tube.

2. The method of claim 1, wherein said defined radial spacing between said outer side of said rod lens and said inner side of said tube is selected in that it lies in a range from approximately 0.05 to 0.3 mm.

3. In the method of claim 2, wherein said radial spacing between said outer side of said rod lens and said inner side of said tube is approximately 0.1 mm.

4. The method of claim 1, wherein said positioning is accomplished with at least three centering elements arranged with a circumferential offset of approximately 120° for each centering aid.

5. The method of claim 1, wherein said centering elements are left in an assemblage of said tube and said rod lens after said adhesive join has been effected.

6. The method of claim 1, wherein elongated bodies are selected for positioning said rod lens, said elongated bodies are set in place extending axially in said spacing between said inner side of said tube and said outer side of said rod lens, said elongated bodies are removed after said adhesive joint is effected.

7. The method of claim 1, wherein elongated bodies are selected for positioning said rod lens, said elongated bodies are set in place extending axially in said spacing between said inner side of said tube and said outer side of said rod lens, and said elongated bodies are left in said tube.

8. The method of claim 1, wherein said centering elements are designed as radially extending centering pins passing through openings in a wall of said tube, said centering pins are removed after said adhesive joins is effected.

9. The method claim 1, wherein at least one opening is provided in a wall of said tube, through which opening an adhesive for effecting said adhesive join is introduced between said outer side of said rod lens and said inner side of said tube, at each adhesive point of said elastic adhesive joint an opening is provided.

10. The method of claim 9, wherein a centering pin passes through said opening through which opening said adhesive is applied, and an outer side of said centering pin is designed in that it can be removed from an adhesive join effected through said opening.

11. The method of claim 10, wherein an outer side of said centering pin is provided with a material repelling said adhesive.

12. The method of claim 11, wherein said centering pin is provided with a conical tip.

13. The method of claim 12, wherein three openings are provided distributed uniforming around a circumference of said tube.

14. The method of claim 1, wherein at least one opening is provided in a wall of said tube, and an adhesive is applied through said opening forming a ring of adhesive enclosing circumferentially said outer side of said rod lens in an area of said opening.

15. The method of claim 1, wherein said centering elements are designed as adhesive dots that can be activated by a particular treatment for deforming it and for forming an adhesive bound between said outer side of said rod lens and said inner side of said tube.

16. The method of claim 15, wherein said particular treatment is a heat treatment.

17. The method of claim 16, wherein said adhesive dots are surrounded by a barrier.

18. The method of claim 17, wherein said adhesive dots are provided on at least one of said outer side of said rod lens and of said inner side of said tube.

19. The method of claim 1, wherein said centering elements are designed as elastic centering elements being adhesively bounded to said inner side of said tube, and said elastic centering elements are adhesively bound to said outer side of said rod lens when effecting said elastic adhesive join.

20. The method claim 1, wherein for mounting a rod lens configured as a dog-bone lens having terminal radial enlargements, said adhesive join is applied adjacent to said enlargements.

21. An endoscope having a tube, in an interior of said tube at least one rod lens is immobilized at at least two points spaced axially apart from one another, said rod lens having an outside diameter dimensioned such, that after an introduction of said rod lens into said tube, an air gap is present between an outer side of said rod lens and an inner side of said tube, and said outer side of said rod lens being arranged at a defined radial spacing from said inner side of said tube, wherein said outer side of said rod lens is immobilized on said inner side of said tube via elastic adhesive joins using an adhesive.

22. The endoscope of claim 21, wherein said adhesive is applied in a form of adhesive dots distributed uniformly around a circumference of said rod lens, for each adhesive join.

23. The endoscope of claim 21, wherein elastic centering elements that are adhesively bounded to said inner side of said tube are applied on said outer side of said rod lens.

24. The endoscope of claim 21, wherein a rod lens configured as a dog-bone lens equipped with radial enlargements is present, said elastic adhesive joins are applied adjacent to said enlargements.

* * * * *